United States Patent [19]

Krantz

[11] Patent Number: 5,383,900
[45] Date of Patent: Jan. 24, 1995

[54] TAPE APPLICATOR

[75] Inventor: Kermit E. Krantz, Misshion Hills, Kans.

[73] Assignee: Medi-Flex Hospital Products, Overland Park, Kans.

[21] Appl. No.: 252,423

[22] Filed: Jun. 1, 1994

[51] Int. Cl.⁶ .............................................. A63B 17/00
[52] U.S. Cl. .................................... 606/215; 221/73; 206/411; 206/389; 602/903
[58] Field of Search ........................ 602/901, 903, 54; 606/215; 206/387, 391, 398, 408, 409, 4.11; 242/55.53, 55.3, 55.4; 221/73

[56] References Cited

U.S. PATENT DOCUMENTS

| | | | |
|---|---|---|---|
| 3,121,021 | 2/1964 | Copeland | 602/903 X |
| 3,737,360 | 6/1973 | Horn | 206/411 X |
| 4,271,962 | 6/1981 | Strepanski | 206/411 |
| 4,531,521 | 7/1985 | Haverstock | 606/215 |
| 4,646,731 | 3/1987 | Brower | 606/215 |
| 4,993,586 | 2/1991 | Taulbee et al. | 206/411 X |

Primary Examiner—Peter A. Aschenbrenner
Attorney, Agent, or Firm—Hovey, Williams, Timmons & Collins

[57] ABSTRACT

A single-use tape applicator includes a pair of sidewalls spaced laterally from one another to define a tape storage enclosure, and two posts extending between the sidewalls and spaced from one another to define a generally oval-shaped run. A closed loop of backing material is supported by the posts and is movable relative to the posts along the run. The length of the loop is substantially equal to the length of the run. A piece of tape coated on one side with an adhesive material is supported and carried on the backing material. The enclosure defines an opening through which the tape is pulled from the backing material and dispensed.

10 Claims, 2 Drawing Sheets

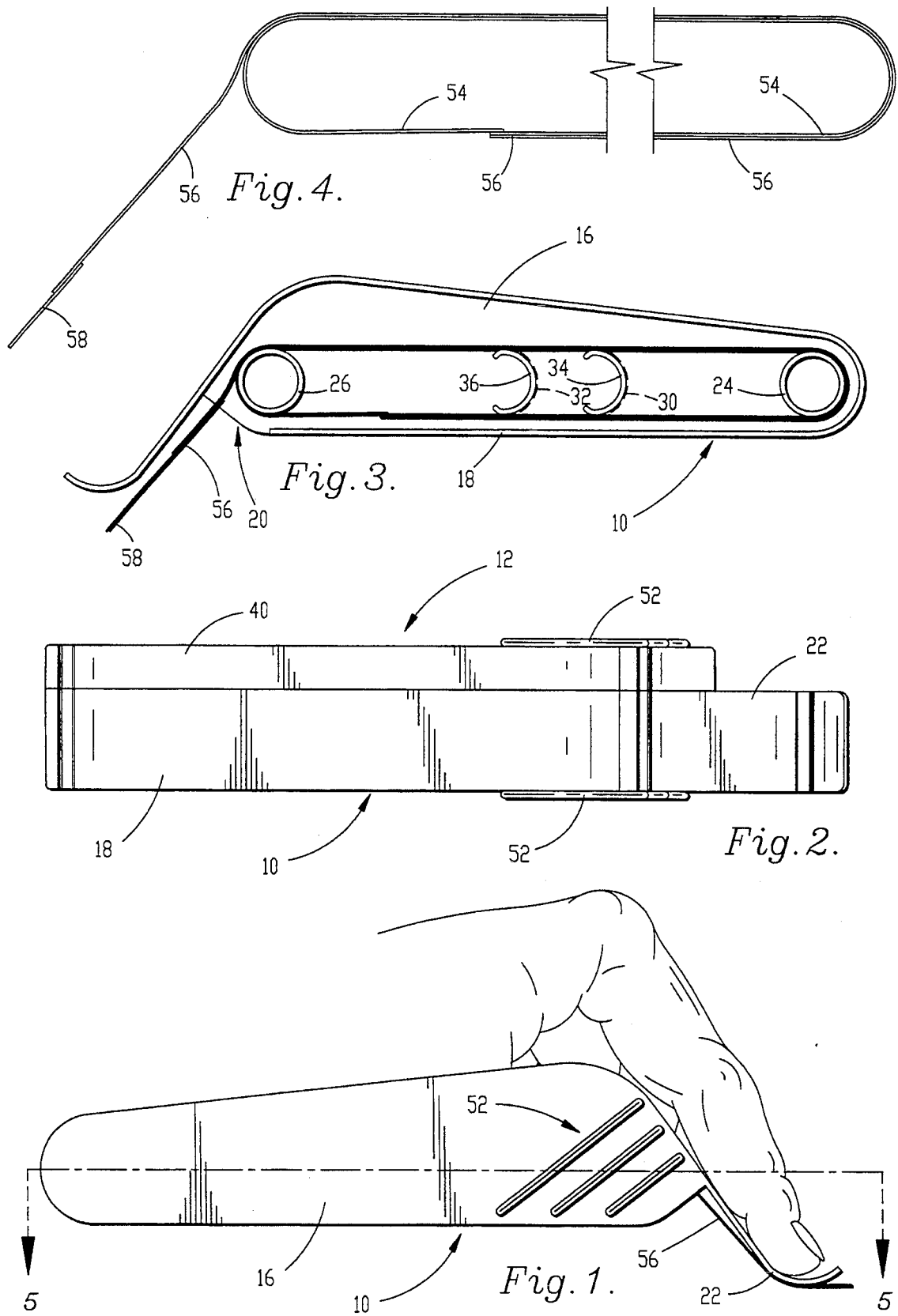

TAPE APPLICATOR

BACKGROUND OF THE INVENTION

1. Field of the Invention

The present invention relates generally to tape applicators and, more particularly, to a single-use, sterile medical applicator for use in dispensing bandages and applying them to the skin of a patient.

2. Discussion of the Prior Art

A skin closure system is disclosed in co-pending U.S. application Ser. No. 08/036,055, filed Mar. 23, 1993, now U.S. Pat. No. 5,336,219 by the present inventor, wherein an elongated bandage is provided which is laid along the length of and bridges an incision in order to hold the edges of the incision together during healing. The subject matter of this prior application is hereby incorporated into the present disclosure by this express reference.

The skin closure system preferably includes two bandages designed for application along either side of the incision, with one of the bandages being provided with a flap that is laid across the incision and adhered to the other bandage in order to close the incision. However, the system may include a single bandage having a construction which permits coverage of the incision.

OBJECTS AND SUMMARY OF THE INVENTION

It is an object of the present invention to provide a tape applicator for use in dispensing bandages of the type disclosed in the aforementioned application. In furtherance of this object, it is a goal of the invention to provide a simple, inexpensive construction that may be sterilized and used once and then be discarded.

At the same time, it is an object of the invention to provide an applicator designed to support a tape of predetermined length, or to alternately support any one of several different tape sizes. In this manner several applicators, each of substantially the same construction, may be loaded with different tape lengths so that a user may select an applicator in which a suitable length of tape is stored for the particular single use to be made of the tape. This provides the same feel to the user regardless of the tape length selected.

Another object of the invention is to provide an applicator that fits easily in the hand of a user while allowing the user to dispense tape with one hand and accurately apply it to a surface along a desired line.

In accordance with these and other objects of the invention evident from the following description of a preferred embodiment, an applicator includes a pair of sidewalls spaced laterally from one another to define a tape storage enclosure, and a pair of posts extending between the sidewalls and being spaced from one another to define a generally oval-shaped run extending between and around the posts. A closed loop of backing material is supported by the posts and is movable relative to the posts along the run. The length of the loop is substantially equal to the length of the run. A piece of tape is provided which is coated on one side with an adhesive material. The tape is of a length less than about the length of the loop of backing material and is supported and carried on the backing material by the adhesive. The enclosure defines an opening through which the tape may be pulled from the backing material and dispensed.

By providing an applicator in accordance with the invention, numerous advantages are achieved. For example, by providing a construction including a pair of posts on which a closed loop of backing material is supported for movement, the backing material stays within the applicator as the tape is pulled from the backing material and dispensed. Thus, it is possible to permit one-handed application of tape from the applicator simply by pressing an exposed end of the tape to a surface and drawing the applicator along a desired line to dispense the tape from the opening.

BRIEF DESCRIPTION OF THE DRAWING FIGURES

A preferred embodiment of the present invention is described in detail below with reference to the attached drawing figures, wherein:

FIG. 1 is a side elevational view of a tape applicator constructed in accordance with the preferred embodiment;

FIG. 2 is a top plan view of the applicator;

FIG. 3 is a side elevational view of a main body of the applicator, illustrating the interior of the body;

FIG. 4 is a fragmentary view of a piece of tape adapted for use in the applicator;

DETAILED DESCRIPTION OF THE PREFERRED EMBODIMENT

A tape applicator constructed in accordance with a preferred embodiment of the present invention is illustrated in FIG. 1, and is particularly adapted for use in dispensing bandages of the type disclosed in co-pending application Ser. No. 08/036,055, noted above.

Figure 10:
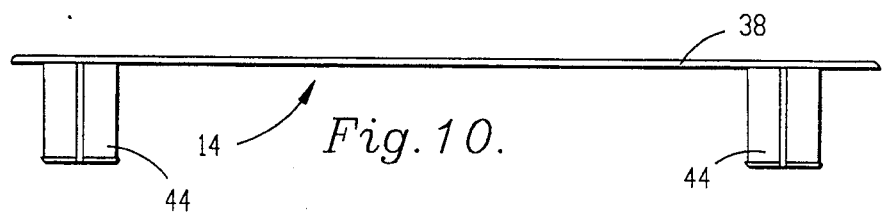
FIG. 10 is a top plan view of the second side cover.
Figure 9:
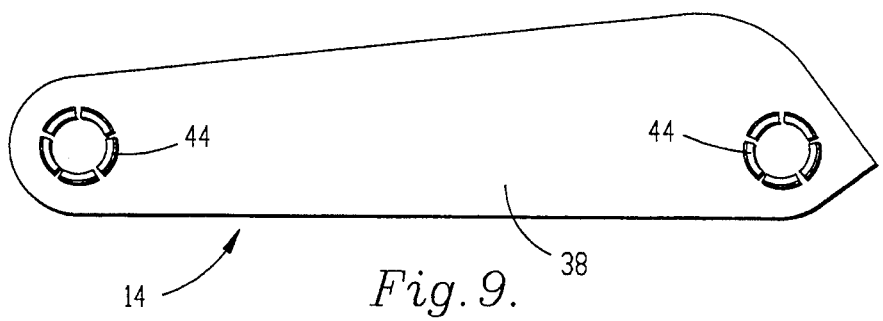
FIG. 9 is a side elevational view of a second side cover of the applicator adapted for use in place of the first side cover.
Figure 8:
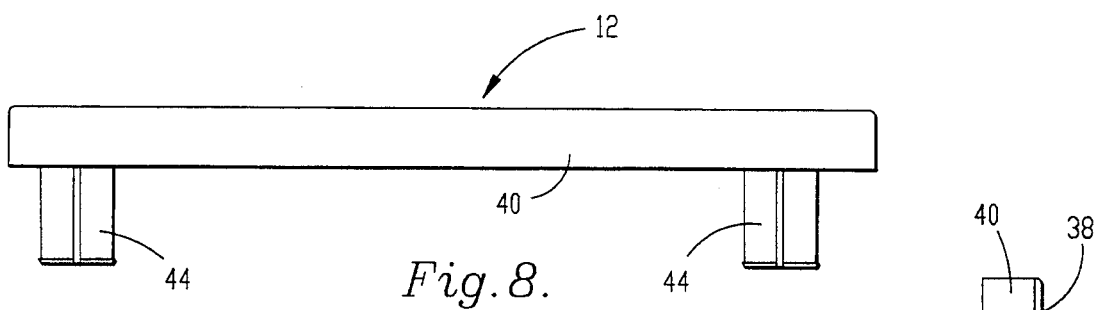
FIG. 8 is a top plan view of the first side cover.
Figure 7:
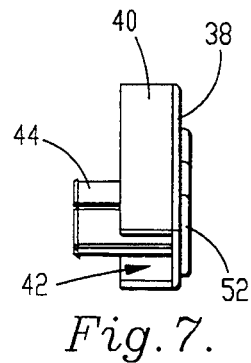
FIG. 7 is an end elevational view of the first side cover.
Figure 6:
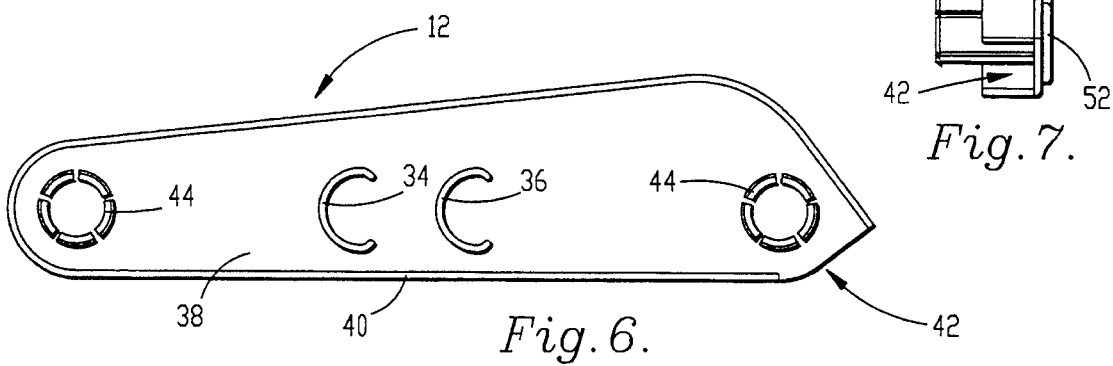
FIG. 6 is a side elevational view of a first side cover of the applicator.
Figure 5:
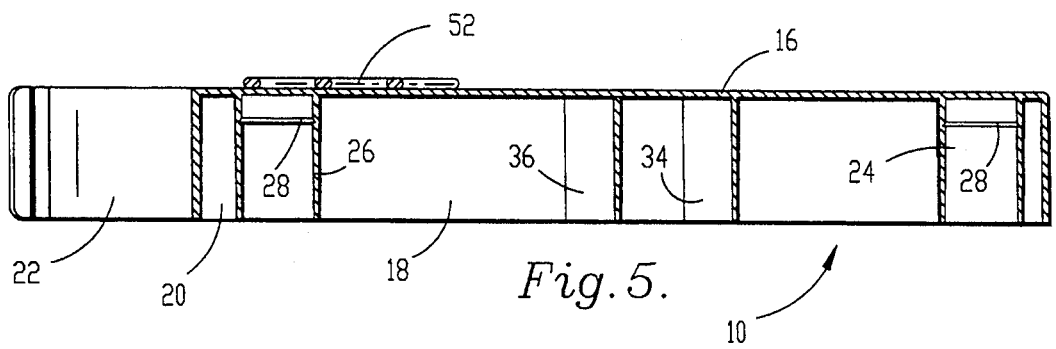
FIG. 5 is a sectional view of the applicator body taken along line 5—5 of FIG. 3.

The applicator is assembled of two elements, a body 10 shown in FIGS. 3 and 5, and a side cover 12 illustrated in FIGS. 6-8. An alternate side cover 14 adapted for use with the body is shown in FIGS. 9 and 10, and is described more fully below. When the body is assembled with either of the side covers 12, 14, they define a tape storage enclosure within which a piece of tape and a backing material, shown in FIG. 4, are supported.

Turning to FIG. 3, the body 10 includes a sidewall 16, and a circumferencial wall 18 extending along and protruding outward from the edge of the sidewall except for at an opening 20 defined at the forward end of the body. The portion of the circumferencial wall extending along the upper edge of the sidewall projects beyond the opening to define a depressor 22 adapted to engage the tape during dispensing. As shown in FIG. 1, the depressor 22 presents an upturned surface adapted to receive the finger of a user so that the user can guide the tape during application, and press the tape against the surface to be taped or bandaged.

A pair of hollow tubular posts 24, 26 are provided on the body and extend laterally from the sidewall 16 by a distance substantially equal to the width of the circumferencial wall 18, as shown in FIG. 5. The posts 24, 26 are substantially identical to one another, and each includes an open interior space adapted to receive either of the side covers 12, 14 so that the body and a side cover may be fastened together during assembly. The interior surface of each post 24, 26 is formed with an annular groove 28 spaced slightly from the sidewall. These annular grooves cooperate with structure on each side cover 12, 14 to define a locking means for securing either of the side covers to the body during assembly.

Returning to FIG. 3, the posts 24, 26 are shown as being spaced from one another to define a generally-oval-shaped run extending between and around the posts. A pair of alternate runs 30, 32, partially shown in dashed lines in FIG. 3, are also defined on the body by a pair of C-shaped support posts 34, 36, each protruding from the sidewall 16 by a distance substantially equal to the width of the circumferencial wall 18. These additional support posts 34, 36 are spaced from each other and from the other posts 24, 26 such that each additional post defines one of the substitute runs 30, 32.

The side cover 12 is illustrated in FIG. 6, and includes a sidewall 38, and a circumferencial wall 40 extending along and protruding outward from the edge of the sidewall except for at an opening 42 defined at the forward end of the side cover. The opening 42 is aligned with the opening 20 in the wall of the body so that the overall width of the openings is large enough to accommo date tape of a width substantially equal to the distance between the sidewalls 16, 38 of the assembled body and cover. The side cover preferably does not include a depressor, but rather is cut off to allow the user to observe application of the tape, e.g. as when a bandage is being applied along or over a surgical incision.

The side cover 12 includes a plurality of fingers 44 aligned with each of the two posts 24, 26 of the body 10, and these fingers are arranged for receipt within the interior of the posts and for engagement with the annular grooves 28. Preferably, the fingers are arranged in circular patterns, each having an outer diameter substantially equal to the distance between the sidewalls 16, 38 formed with a radially outward protruding lip 46, as shown in FIG. 7, that snap fits into the groove 28 of one of the posts when the side cover is assembled on the body. Returning to FIG. 6, the side cover 12 also includes a pair of C-shaped support posts 48, 50 similar to and aligned with the support posts 34, 36 of the body 10. These support posts help define the alternate runs 32, 34. A shown in FIG. 8, the support posts 48, 50 are only as wide as the circumferencial wall 40, and abut the posts 34, 36 end to end when the side cover 12 is assembled on the body 10.

The side cover 12 is shown assembled on the body 10 in FIG. 2, wherein the enclosure defined by the elements is shown as including a width equal to the overall width of the two circumferencial walls 18, 40. Each sidewall includes a plurality of ribs 52 adjacent the opening for facilitating handling of the applicator, and the apparatus is shaped to easily fit within the palm of a user's hand.

The second side cover 14 is illustrated in FIGS. 9 and 10, and is similar to the side cover 12 in that it includes a sidewall 38 and a plurality of fingers 44 aligned with each of the posts 24, 26. However, the side cover 14 differs from the cover 12 in that the cover 14 does not have a circumferencial wall or any C-shaped support posts. By assembling the cover on the body, an apparatus results which has a width smaller than the width of the apparatus of FIG. 2, and tapes of smaller widths may be handled. As will be understood, the body 10 may be easily adapted for use with side covers of different widths than those shown in order to adapt the apparatus for different uses.

The tape assembled for use in the apparatus is shown in FIG. 4, and includes a closed loop of backing material 54, a piece of tape 56, and a tab-defining means 58 for defining a tab at one end of the tape between the tape and the backing material for permitting the tape to be separated from the backing material to initiate removal.

The backing material 54 is preferably Mylar or other suitable material capable of providing mechanical support to the tape, and is formed into a closed loop that is adapted to be supported by the posts for movement along the run. The length of the loop is substantially equal to the length of the run so that the loop can easily slide over and around the posts when the tape is pulled through the opening. Thus, the backing material functions as a carrier for carrying the tape toward the opening and for drawing itself back into the enclosure as the tape is dispensed. Preferably, the backing material is formed into a closed loop by adhering or welding the ends of a strip of backing material together during manufacture of the tape.

The tape 56 is coated on one side with a conventional adhesive material, and is of a length less than or about equal to the length of the loop of backing material so that the entire length of tape is supported and carried on the backing material by the adhesive. The tab-defining means 58 preferably includes a small length of backing material that is adhered to one end of the tape between the tape and the loop of backing material. By providing this construction, the tab 58 separates the tape end from the backing material to permit the end to be gripped by the user and pulled from the opening. The tab may be cut or otherwise removed from the tape so that the tape is prepared for application.

Thereafter, the tape is simply applied to a desired surface, and the applicator is drawn across the surface while the user guides the tape and presses down on the depressor 22. Thus, the tape is forced against the surface and adheres thereto.

As mentioned above, the skin closure system with which the applicator is adapted for use preferably includes two bandages designed for application along either side of the incision, with one of the bandages being provided with a flap that is laid across the incision and adhered to the other bandage in order to close the incision. In order to accommodate this type of bandage system, a single closed loop of backing material is provided which has a width equal to the combined width of the bandages, and the side cover is used in the assembly to increase the overall width of the applicator. The two bandages are thus adhered side-by-side on the single loop of backing material and are dispensed together from the applicator, with each running along a side of the incision to be covered. Thereafter, the flap of the one bandage may be folded over onto the other to complete closure of the incision.

When the applicator is to be used with a single piece of tape or a single bandage, the side cover 14 is used, and the tape is supported on a loop of backing material having a width equal to the width of the tape. Likewise, when the applicator is to be loaded with a length of tape that is shorter than the length of the run extending around the posts, the closed loop of the backing material is formed in a length corresponding to the length of one of the shorter runs defined by the C-shaped support posts. Thus, a single applicator design is capable of accommodating several different widths and lengths of tape.

By constructing an applicator in accordance with the present invention, an apparatus results which enables a person applying tape to accurately dispense the tape single-handedly without having to use a second hand to gather up backing material as it is shed from the tape. This advantage results from the provision of a closed loop of backing material that is drawn back into the enclosure defined by the apparatus as tape is dispensed. Thus, the backing material not only supports the tape during storage, but conveys the tape to the opening in the applicator during use.

Although the invention has been described with reference to the preferred embodiment illustrated in the attached drawing figures, it is noted that substitutions may be made and equivalents employed herein without departing from the scope of the invention as recited in the claims.

What is claimed is:

1. A tape applicator comprising:
   a pair of sidewalls spaced laterally from one another to define a tape storage enclosure;
   a pair of posts extending between the sidewalls and being spaced from one another to define a generally oval-shaped run extending between and around the posts;
   a closed loop of backing material supported by the posts and being movable relative to the posts along the run, the length of the loop being substantially equal to the length of the run; and
   a piece of tape coated on one side with an adhesive material, the tape being of a length less than about the length of the loop of backing material and being supported and carried on the backing material by the adhesive, the enclosure defining an opening through which the tape may be pulled from the backing material and dispensed.

2. A tape applicator as recited in claim 1, further comprising a circumferencial wall extending between the sidewalls and protruding beyond the opening in the enclosure to define a depressor adapted to engage the tape during dispensing.

3. A tape applicator as recited in claim 1, wherein the posts are hollow and tubular in shape, and are formed on one of the sidewalls, the other sidewall being formed with a plurality of fingers protruding into the posts, the posts and fingers together including locking means for securing the fingers to the posts and holding the sidewalls together once assembled.

4. A tape applicator as recited in claim 1, further comprising at least one additional support post extending between the sidewalls and being spaced from the other posts, the additional support post defining a substitute run so that loops of at least two different lengths may be alternately supported in the applicator.

5. A tape applicator as recited in claim 4, wherein two additional support posts are provided so that loops of three different lengths may be alternately supported in the applicator.

6. A tape applicator as recited in claim 1, wherein the backing material is formed of Mylar.

7. A tape applicator as recited in claim 1, further comprising a tab-defining means for defining a tab at one end of the tape between the tape and the backing material for permitting the tape to be separated from the backing material to initiate removal.

8. A tape applicator as recited in claim 1, wherein the tape is a bandage adapted for medical use, and includes a fabric layer about 1–5 mils thick, a support layer less than about 1 mil thick retained on the fabric layer, and an exposed adhesive layer.

9. A tape applicator as recited in claim 1, wherein the tape has a width substantially equal to the width of the backing material.

10. A tape applicator as recited in claim 1, wherein the tape has a width less than the width of the backing material so that at least two pieces of tape may be retained side-by-side on the backing material.

* * * * *